(12) United States Patent
Medvedev

(10) Patent No.: US 11,712,052 B2
(45) Date of Patent: Aug. 1, 2023

(54) SYSTEMS AND METHODS FOR CONTINUOUS FLOW STERILIZATION

(71) Applicant: OWS AGRI LIMITED, London (GB)

(72) Inventor: Dmitry Medvedev, Fort Worth, TX (US)

(73) Assignee: OWS AGRI LIMITED, London (GB)

( * ) Notice: Subject to any disclaimer, the term of this patent is extended or adjusted under 35 U.S.C. 154(b) by 248 days.

(21) Appl. No.: 16/767,329

(22) PCT Filed: Feb. 9, 2018

(86) PCT No.: PCT/US2018/017601
§ 371 (c)(1),
(2) Date: May 27, 2020

(87) PCT Pub. No.: WO2019/156679
PCT Pub. Date: Aug. 15, 2019

(65) Prior Publication Data
US 2021/0127716 A1    May 6, 2021

(51) Int. Cl.
*A23B 9/22* (2006.01)
*A23L 3/00* (2006.01)
(Continued)

(52) U.S. Cl.
CPC .......... *A23L 3/34095* (2013.01); *A23B 9/22* (2013.01); *A23L 3/001* (2013.01); *A23L 3/003* (2013.01);
(Continued)

(58) Field of Classification Search
None
See application file for complete search history.

(56) References Cited

U.S. PATENT DOCUMENTS 3,700,468 A   10/1972   Shore et al.
4,507,253 A    3/1985   Wiesmann
(Continued)

FOREIGN PATENT DOCUMENTS

DE       4342624 C1    6/1995
KR   20010055638 A    7/2001

OTHER PUBLICATIONS

International Search Report and Written Opinion for the International Patent Application No. PCT/US18/13797, dated May 10, 2018, 7 pages.

(Continued)

*Primary Examiner* — Levon J Shahinian
(74) *Attorney, Agent, or Firm* — KDW Firm PLLC

(57) ABSTRACT

A continuous flow sterilization system includes an inclined treatment chamber having a first end and a second end. An ozone generator generates a flow gas containing ozone; an input opening to receive a bulk material into the treatment chamber. An input port is provided for introducing the flow gas containing of ozone into the treatment chamber. A first sensor measures a level of ozone in the gas output of the treatment chamber. The other sensors measure ozone concentration and temperature within the treatment chamber. An output opening provides an exit for the bulk material. An output port provides an exit for the flow gas. An auger is disposed within the treatment chamber to move the bulk material through the treatment chamber.

12 Claims, 3 Drawing Sheets

(51) Int. Cl.
- *A23L 3/3409* (2006.01)
- *A23L 3/3445* (2006.01)
- *A61L 2/20* (2006.01)
- *A61L 2/26* (2006.01)
- *C01B 13/10* (2006.01)

(52) U.S. Cl.
CPC ............. *A23L 3/3445* (2013.01); *A61L 2/202* (2013.01); *A61L 2/26* (2013.01); *C01B 13/10* (2013.01); *A61L 2202/122* (2013.01); *A61L 2202/13* (2013.01); *A61L 2202/14* (2013.01); *A61L 2202/20* (2013.01)

(56) References Cited

U.S. PATENT DOCUMENTS

| | | | |
|---|---|---|---|
| 4,549,477 | A | 10/1985 | McCabe, Jr. |
| 4,732,480 | A | 3/1988 | Fortunato et al. |
| 5,334,355 | A | 8/1994 | Faddis |
| 5,420,432 | A | 5/1995 | Manook et al. |
| 5,632,333 | A | 5/1997 | Imamura et al. |
| 5,868,999 | A | 2/1999 | Karlson |
| 5,972,714 | A | 10/1999 | Roland et al. |
| 6,171,625 | B1 | 1/2001 | Denvir et al. |
| 6,485,769 | B2 | 11/2002 | Audy et al. |
| 6,518,574 | B1 | 2/2003 | Castleman |
| 6,673,248 | B2 | 1/2004 | Chowdhury |
| 6,764,659 | B2 | 7/2004 | Perlov et al. |
| 7,375,348 | B1 | 5/2008 | Sickenberger et al. |
| 8,298,418 | B2 | 10/2012 | Liechti et al. |
| 2001/0042843 | A1 | 11/2001 | Cox et al. |
| 2002/0025364 | A1* | 2/2002 | Audy ................. A23L 3/358 422/120 |
| 2003/0030011 | A1 | 2/2003 | Brown et al. |
| 2004/0018630 | A1 | 1/2004 | Birks et al. |
| 2004/0052702 | A1 | 3/2004 | Shuman et al. |
| 2004/0097021 | A1 | 5/2004 | Augusto et al. |
| 2004/0241868 | A1 | 12/2004 | Cox et al. |
| 2005/0103723 | A1 | 5/2005 | Wilkins et al. |
| 2005/0160791 | A1 | 7/2005 | Kung |
| 2006/0240558 | A1 | 10/2006 | Zhao |
| 2008/0116054 | A1 | 5/2008 | Leach et al. |
| 2008/0304048 | A1 | 12/2008 | Tormod |
| 2009/0120473 | A1 | 5/2009 | Lynn |
| 2009/0302230 | A1 | 12/2009 | Birks et al. |
| 2010/0027016 | A1 | 2/2010 | Birks et al. |
| 2010/0061885 | A1 | 3/2010 | Harley |
| 2010/0159601 | A1 | 6/2010 | Patton |
| 2010/0212406 | A1 | 8/2010 | Browne et al. |
| 2011/0147580 | A1 | 6/2011 | Bell et al. |
| 2011/0164245 | A1 | 7/2011 | Eikelmann et al. |
| 2011/0201123 | A1 | 8/2011 | Watson et al. |
| 2012/0006098 | A1 | 1/2012 | Degner et al. |
| 2012/0135396 | A1 | 5/2012 | McDevitt et al. |
| 2013/0045496 | A1 | 2/2013 | Jansen |
| 2013/0270429 | A1 | 10/2013 | Bilenko et al. |
| 2013/0292581 | A1 | 11/2013 | Russell et al. |
| 2014/0034840 | A1 | 2/2014 | Davenport et al. |
| 2014/0106463 | A1 | 4/2014 | Wald et al. |
| 2015/0070889 | A1 | 3/2015 | Sooferian |
| 2015/0362426 | A1 | 12/2015 | Nishino et al. |
| 2015/0377772 | A1 | 12/2015 | Birks et al. |
| 2016/0103089 | A1 | 4/2016 | Boyette et al. |
| 2016/0187214 | A1 | 6/2016 | Al-Hemyari |
| 2017/0115272 | A1 | 4/2017 | Rihani et al. |
| 2017/0219479 | A1 | 8/2017 | Bilenko et al. |
| 2019/0056317 | A1 | 2/2019 | Clausen et al. |

OTHER PUBLICATIONS

International Search Report and Written Opinion for the International Patent Application No. PCT/US18/015019, dated Apr. 6, 2018, 10 pages.

International Search Report and Written Opinion for the International Patent Application No. PCT/US18/14768, dated Apr. 5, 2018, 8 pages.

Nikoleav et al., "Atmospheric Ozone Concentration Measurement by UV Light-Emitting Diode Radiation Absorption" Bulletin of the Lebedev Physics Insitute. 2013, vol. 40 (2), pp. 50-53.

International Search Report and Written Opinion for the International Patent Application No. PCT/US18/14841, dated Mar. 29, 2018, 8 pages.

International Search Report and Written Opinion for the International Patent Application No. PCT/US18/15846, dated Mar. 29, 2018, 9 pages.

International Search Report and Written Opinion for the International Patent Application No. PCT/US18/17601, dated May 7, 2018, 7 pages.

* cited by examiner

SYSTEMS AND METHODS FOR CONTINUOUS FLOW STERILIZATION

This is a national stage application filed under 35 U.S.C. § 371 of international application PCT/US2018/017601, filed Feb. 9, 2018, the entirety of which application is hereby incorporated by reference herein.

FIELD OF THE DISCLOSURE

The present disclosure relates generally to continuous flow sterilization techniques, and more particularly to systems and methods for continuous flow sterilization of bulk materials using ozone.

BACKGROUND OF THE DISCLOSURE

A major problem in the food industry is the growth of bacterial substances and microorganisms that can occur in grain or feed for livestock. If the grain or feed becomes contaminated anywhere within the production and delivery process it can then infect livestock and cause diseases to occur. To avoid this problem, it is necessary to ensure that the feed and feeder are sanitized properly. There are several procedures and methods currently in use to mitigate the contamination potential of livestock feed. These include the introduction of chemical bactericides, fungicides and other liquids which can be hazardous, carcinogenic, and polluting. Alternative methods are being pursued to eliminate the use of these chemical agents such as heat processing and UV light exposure. But these have multiple drawbacks such as cost, efficacy and difficulty in application due to the flowing nature of these feeds and the desire to accomplish the disinfection on a continuous versus a batch basis. Ozone has been proven to be a high-quality disinfecting agent that is extremely effective in killing disease causing bacteria. There have been attempts at deploying ozone systems for livestock feed, but a viable system has not been developed.

SUMMARY

This summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The disclosure describes a continuous flow Ozone ($O_3$) Sterilization system and method for disinfecting bulk materials, such as livestock feed, on a continuous basis. The system can have several variable parameters and monitoring functions that will allow for analysis of different types of bulk material, such as feed, to be treated; ozone concentrations needed for adequate sterilization; and other factors necessary for upscaling the technology to a production-ready unit which can be deployable in the marketplace.

A continuous flow sterilization system is disclosed. The system can include a treatment chamber having a first end and a second end; an ozone generator to generate ozone; an input opening located proximate the first end of the treatment chamber, the input opening configured to receive a bulk material into the treatment chamber; an input port located proximate the first end of the treatment chamber, the input port configured to introduce the flow of gas containing ozone into the treatment chamber, an output opening located proximate the second end of the treatment chamber, the output opening configured to provide an exit for the bulk material received into the treatment chamber via the input opening; an output port located proximate the second end of the treatment chamber, the output port configured to exhaust the flow of gas containing ozone from the treatment chamber, and a material movement mechanism located within the treatment chamber and generally extending from the input opening to the output opening, the material movement mechanism configured to move the bulk material from the input opening to the output opening. The treatment chamber may be inclined such that the second end of the treatment chamber is higher than the first end of the treatment chamber.

The treatment chamber may be selectively adjustable from a first inclined position to a second inclined position. A support structure may be provided for supporting the treatment chamber, the support structure being arranged and configured to allow selective adjustability of an angle of inclination of the treatment chamber.

The system may include a fan in communication with the output port, the fan configured to create a negative pressure within the treatment chamber to cause the flow of ozone introduced at the first end via the input port to exit at the second end via the output port.

The system may include a filter, the filter configured to perform one of: convert the ozone into oxygen for release into the local atmosphere, or remove toxicity from the flow of gas before it is emitted into the atmosphere.

The system may include a plurality of sensors in communication with the treatment chamber for monitoring one or more parameters. The plurality of sensors may include at least one first sensor to measure a level of ozone in the gas output of the treatment chamber; and at least one second sensor to measure a temperature within the treatment chamber.

The system may include a user interface to display the level of ozone and the temperature within the treatment chamber.

The material movement mechanism may be an auger located within the treatment chamber, the auger extending from the input opening to the output opening for moving the bulk material from the input opening to the output opening. The auger may have an outer diameter and the treatment chamber includes an inner diameter, the outer diameter of the auger being substantially the same as the inner diameter of the treatment chamber. The auger may include a central shaft and a helical screw, the screw being rotatably disposed within the treatment chamber. The helical screw may comprise a plastic material.

The system may include a drive motor coupled to an end of the shaft for rotating the helical screw. The drive motor may be configured to rotate the helical screw in a first rotational direction and in a second rotational direction so that the bulk material within the treatment chamber can be moved in either direction. The drive motor may be a variable speed drive motor so that a rotational speed can be adjusted.

The system can include an air or oxygen source for suppling a flow of feed gas to the ozone generator, the ozone generator being configured to convert the part of oxygen into the ozone. The ozone may have a concentration between 1 parts per million (PPM) to 30.000 PPM ozone, and a rate of flow between about 10 Liter per hour (L/hr) to about 10.000 L/hr.

A method for continuous sterilization of a bulk material is also disclosed. The method may include generating of ozone from the gas containing oxygen; introducing the flow gas containing ozone into a treatment chamber, wherein the treatment chamber has first and second ends, the ozone introduced proximate the first end; the second end positioned above the first end so that the treatment chamber is inclined; contacting the ozone with the bulk material as the bulk material is being moved through the treatment chamber, measuring an ozone level in the gas output of the treatment chamber and ozone level or a temperature within the treatment chamber; and creating a negative pressure within the treatment chamber to exhaust the flow of ozone out of the treatment chamber proximate the second end.

In use, the method sterilizes the bulk material as the bulk material is moved through treatment chamber with the flow of ozone, the sterilizing occurring through the contacting of the of ozone with the bulk material.

In one embodiment, the speed that the bulk material moves through the treatment chamber may be adjusted, at least in part, on the measured ozone level in the gas output of the treatment chamber and ozone level ozone level or temperature within the treatment chamber. The method may also filter ozone before the flow of gas is released into the atmosphere.

BRIEF DESCRIPTION OF THE DRAWINGS

By way of example, exemplary embodiments of the disclosed device will now be described, with reference to the accompanying drawings, in which.

DETAILED DESCRIPTION

Figure 1:
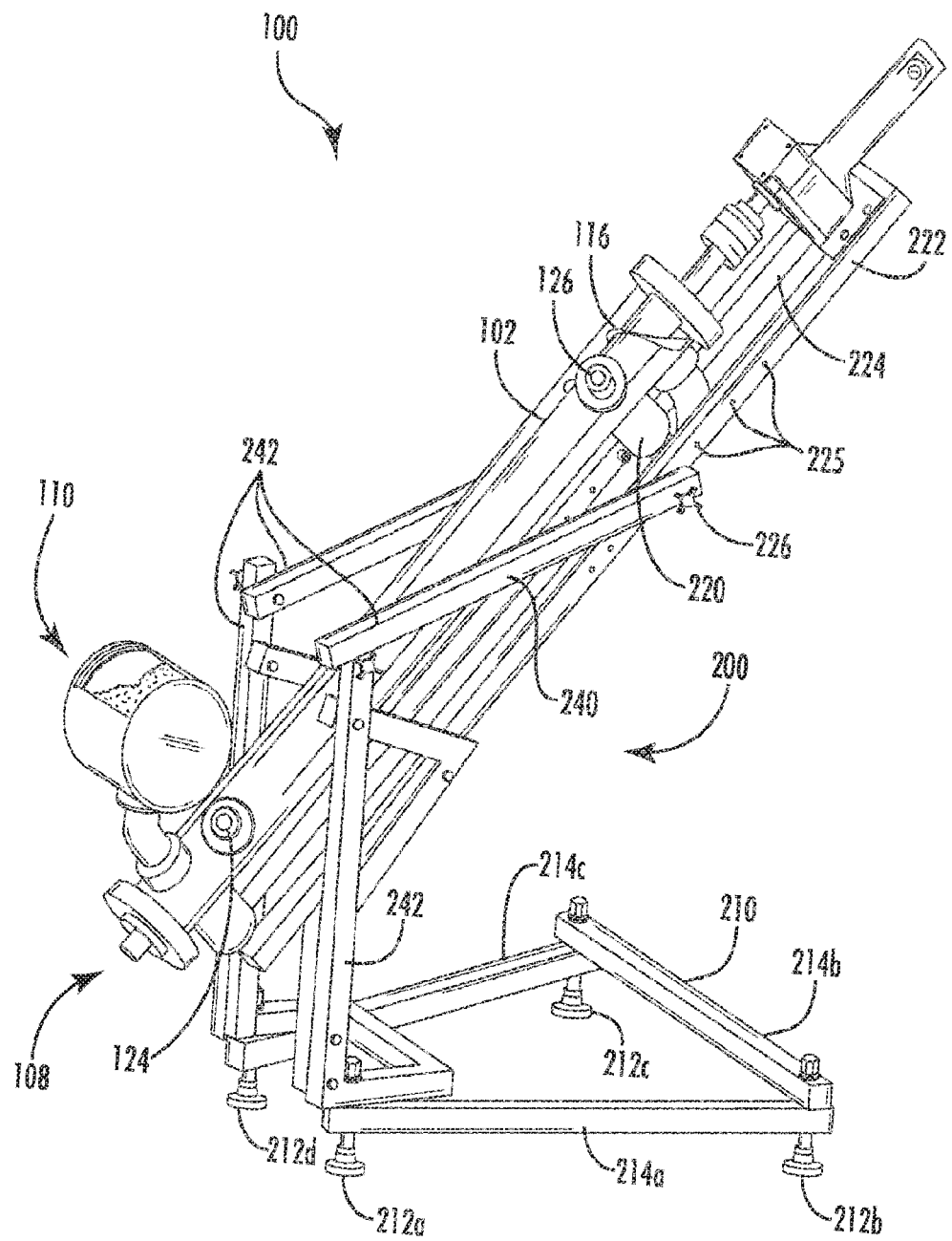
FIG. 1 is a perspective view of an example embodiment of a continuous flow sterilization system, the continuous flow sterilization system illustrated in a first position.

The following disclosure is intended to provide exemplary embodiments of the disclosed system and method, and these exemplary embodiments should not be interpreted as limiting. One of ordinary skill in the art will understand that the elements disclosed may easily be reordered and manipulated into many configurations, provided they are not mutually exclusive. As used herein, "a" and "an" may refer to a single or plurality of items and should not be interpreted as exclusively singular unless explicitly stated.

Ozone ($O_3$) is a colorless, unstable toxic gas with a pungent odor and powerful oxidizing properties, formed from oxygen. It differs from normal oxygen ($O_2$) in having three atoms in its molecule ($O_3$). Ozone, as a gas and solubilized in water, has powerful disinfecting qualities and thus it can be a highly effective sanitizer for treating contaminants such as E-*coli, listeria, salmonella*, and *campylobacter*. Further, the strong oxidizing properties of ozone can destroy a wide range of pathogens, including fungi and prions. Ozone may be applied during food processing to safely sanitize the food and/or food processing environment. In some embodiments of the disclosure ozone will be used as a sanitizing agent.

Ozone can destroy a wider variety of organisms than other cleaning agents, such as chlorine or formaldehyde, without creating harmful by-products that could be potentially dangerous. The exposure treatment time for ozone, is also considerably lower than those of other treatment methods. It is for these reasons that ozone is a preferred choice as a disinfecting agent. In some embodiments ozone can be used to disinfect edible products such as livestock fee. The disclosed system and methods are configured to engulf the particles of feed (in one embodiment) with a measurable and variable level of ozone to sanitize the feed to an effective level. The system and method may use ambient or dry air to create the ozone gas or, for higher levels of ozone, an oxygen supply can be used. There is also an option of employing a bench-top oxygen concentrator, thereby eliminating the need for a supply of oxygen.

The generated ozone may be passed through a flow sensor into a treatment chamber, such as, for example, a polycarbonate tube which has an opening on one end, to receive the feed, and an opening on the opposite end, where the treated feed exits—all on a continuous basis. Along the treatment chamber may be a series of sensors, for example, temperature and ozone sensors, to record levels along the length of the exposure area. The feed may be moved from the entrance opening of the treatment chamber to the exit by any means now know or hereafter developed. For example, the treatment chamber may include an auger with a variable speed motor, to allow for variations in rotational speed. This provides variability in the dwell time of the feed in the treatment chamber to test levels of ozone exposure. The auger may include a central steel cylindrical shaft, for strength, completely embedded within a thermoformed plastic helical flight. The helical flight, when rotated, causes the feed to move from the entrance opening to the exit end of the treatment chamber.

The preferred helical flight material used may be plastic due to its resistance to the oxidizing effects of ozone. To allow for continuous flow treatment, as opposed to batch treatment, the treatment chamber includes openings at both ends to receive and deliver the feed continuously. In such an open system, ozone could be emitted into the atmosphere, which would be undesirable. To obviate this problem, a filter and negative pressure vacuum system may be incorporated in the continuous flow sterilization system to draw away the ozone gas while maintaining continuous treatment flow, although other means for preventing ozone from escaping into the atmosphere are envisioned.

Figure 2A:
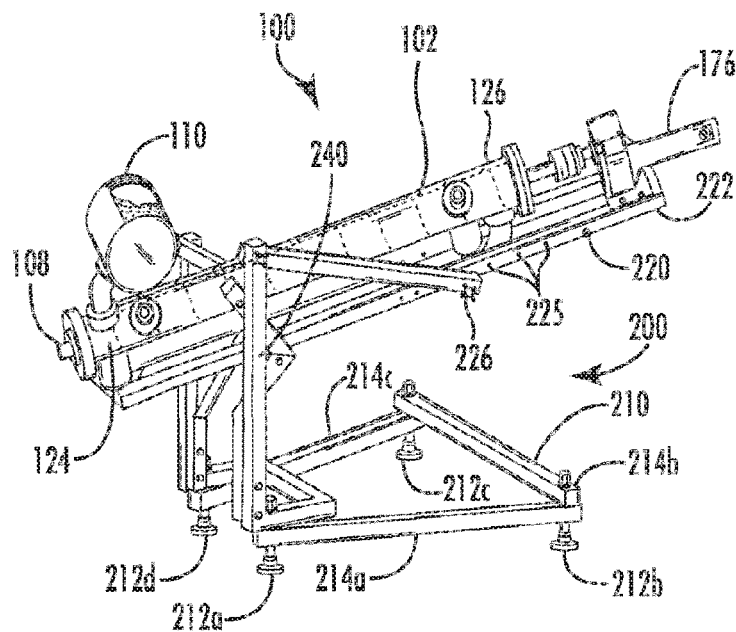
FIG. 2 is a perspective view of the continuous flow sterilization system shown in FIG. 1, the continuous flow sterilization system illustrated in a second position.
Figure 2B:
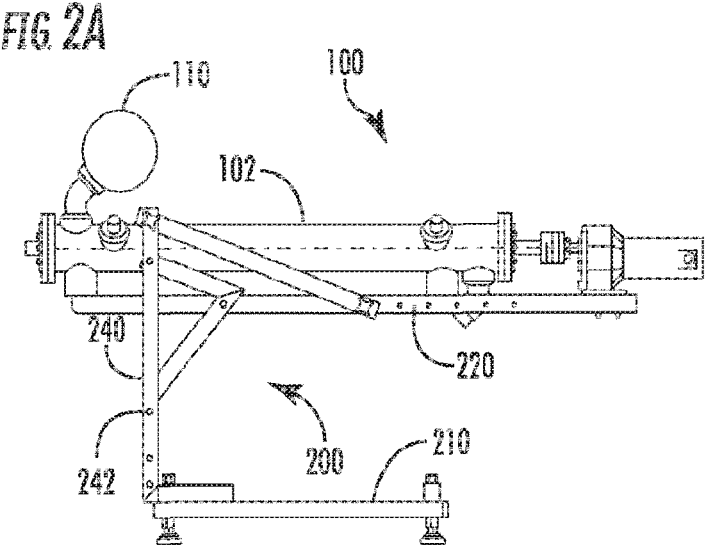
Figure 2C:
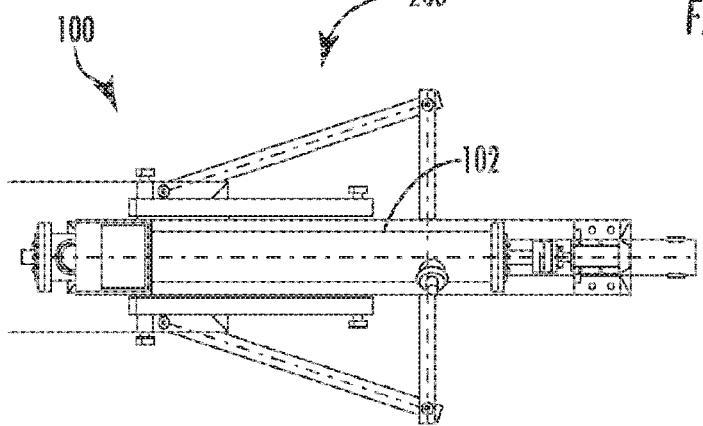
Figure 3:
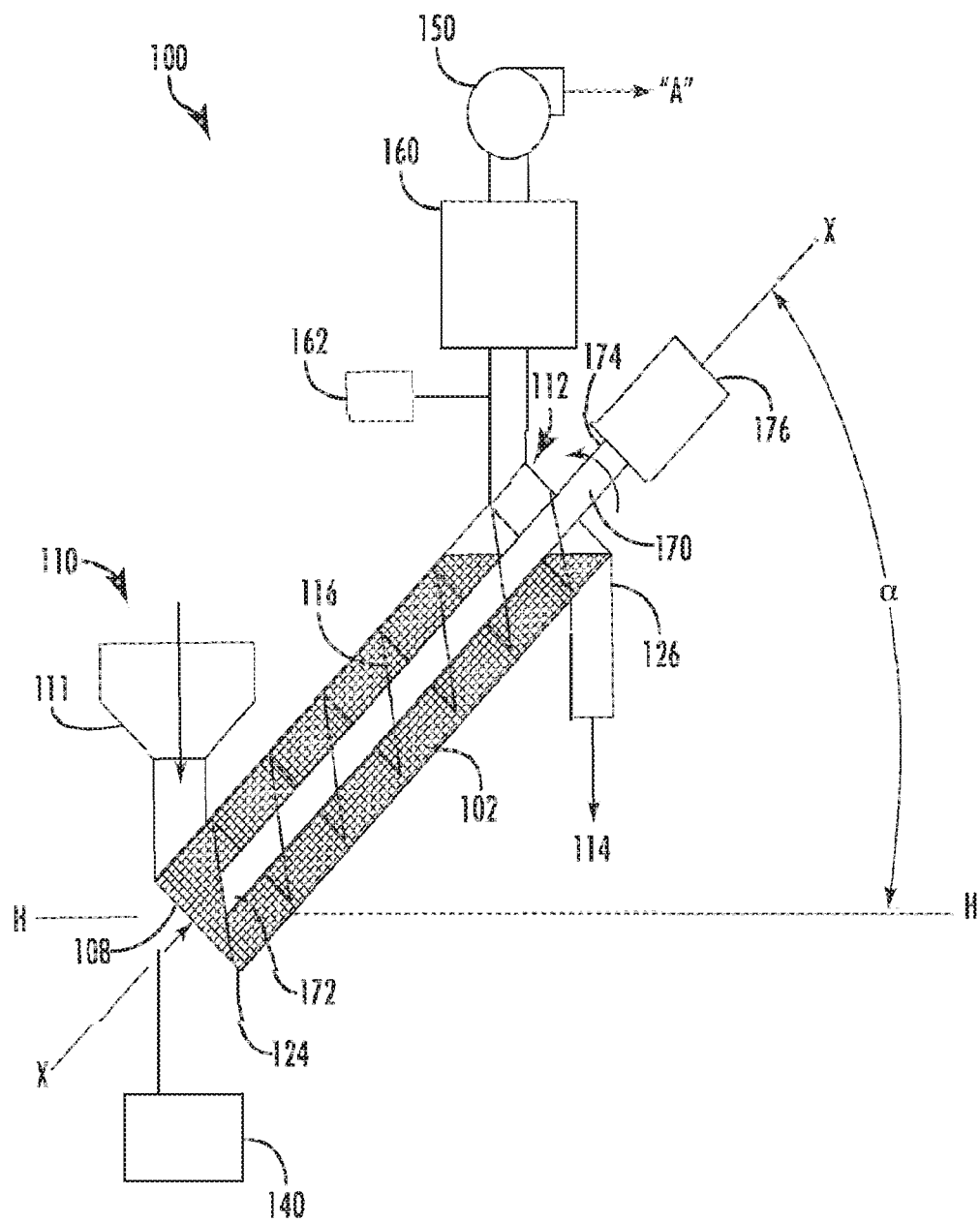
FIG. 3 is a schematic view of the continuous flow sterilization system shown in FIG. 1.

Referring to FIGS. 1-3, an example embodiment of a continuous flow sterilization system 100 consistent with a non-limiting, exemplary embodiment of the present disclosure is shown.

The continuous flow sterilization system 100 enables a continuous stream of bulk material to be subjected to an ozone-based sterilization process. The continuous flow sterilization system 100 can operate to safely and effectively sterilize bulk materials disposed within a treatment chamber 102 in a continuous manner. In some embodiments, the bulk materials may include food products such as animal feed. In other embodiments, the bulk materials may include bedding for livestock. In any case, the materials may be collectively referred to herein as bulk material for the sake of clarity without the intent to limit. It will be appreciated, however, that the disclosure is not limited in this respect.

Applicants however have discovered that while bulk material, especially grains or livestock, are capable of absorbing ozone efficient, to ensure that the bulk material, especially grains, is effectively decontaminated, the continuous flow sterilization system 100 should be arranged and configured to ensure that the ozone/air mixture in the treatment chamber 102 is properly passed through the bulk material (e.g., grains).

To ensure that an effective amount of ozone is passed through the bulk material (e.g., grains) in the treatment chamber 102, at least a portion of the treatment chamber 102 can be arranged and configured to be substantially filled with bulk material (e.g., grain) without a substantial amount of empty space, especially above the layer of bulk material in the treatment chamber. In addition, the treatment chamber 102 may be arranged and configured to ensure that ozone flow passes through the bulk material as the bulk material is being moved within the treatment chamber.

Referring FIGS. 1-3, the continuous flow sterilization system 100 may include a treatment chamber 102 that is inclined, and in some embodiments, is selectively inclined from, for example, a horizontal position (as shown in FIGS. 2A-2CC) to an inclined position (as shown in FIGS. 1 and 3). By selectively inclined, it is meant that the angle of inclination "α" of the treatment chamber 102, and hence the auger 116 (FIG. 3) located therein, can be adjusted by the user as desired so that a longitudinal axis X-X of the treatment chamber is oriented at an oblique angle with respect to the horizontal plane. The angle of inclination can be adjusted by any mechanism now known or hereafter developed. For example, as shown in FIGS. 1-2C, the continuous flow sterilization system 100 may include a support structure 200 for supporting the continuous flow sterilization system 100. The support structure 200 may enable the angle of inclination "α" of the treatment chamber 102 and the auger 116 located thereon, to be adjusted by a user. In this manner, the continuous flow sterilization system 100 can be adjusted to ensure that any bulk material that is received within the treatment chamber 102 via the input opening 110 is collected and tightly packed at the first end 124 of the treatment chamber 102 where it is gathered and moved by the auger 116.

As previously mentioned, the treatment chamber 102 may be arranged and configured to ensure that gas containing ozone flow passes through the bulk material within the chamber. To this end, the outer diameter of the auger 116 (e.g., the outer diameter of the helical screw forming the auger) can be substantially similar to the inner diameter of the treatment chamber 102 in which the auger 116 resides. That is, preferably, the outer edge of the auger 116 is in very close proximity to the inner surface of the treatment chamber 102 so as to minimize the clearance between the outer edge of the auger and the inner surface of the treatment chamber. In this manner, ozone flow traveling from the input port 108 to the output port 112 is prevented from bypassing the bulk material (i.e., by flowing between the outer edge of the augur and the inner diameter of the treatment chamber), and thus forces the ozone to mix with the bulk material. That is, the amount of ozone flow that can travel from the input port 108 to the output port 112, above the bulk material, without mixing with the bulk material is substantially minimized or eliminated.

The continuous flow sterilization system 100 may include an ozone generator 140 (FIG. 3), a treatment chamber 102, a fan 150, an ozone destructor 160, and an ozone concentration measurement system 162. In one embodiment, the ozone concentration measurement system 162 is coupled to the exhaust flow (e.g., gas which is removed from the treatment chamber 102) so that the user can measure the concentration of ozone leaving the treatment chamber 102 to determine the effectiveness of the treatment process.

Grains and other materials are able to efficiently absorb ozone up to a saturation limit. If the ozone present in the treatment chamber 102 is not sufficient to saturate all grains traveling through system, then ozone concentration at the output of system will be practically zero. In such a case, ozone capacity may be increased, and after reaching of saturation limit characteristic for a particular grain type, ozone concentration at the output of the system will increase dramatically up to a concentration comparable with the concentration at the input to the system. After that point it can be assumed that all grains are saturated by ozone and the sterilization process is complete. Typical absorption ability of grains is about 50 g of ozone per 1000 kg of grains.

These and other components of the continuous flow sterilization system 100 can interoperate to safely and effectively sterilize bulk materials disposed within the treatment chamber 102 in a continuous manner, as described herein.

As previously mentioned, the ozone generator generates ozone from air. In some embodiments, the ozone generator 140 may receive an oxygen flow from an oxygen source (not shown). In some embodiments, the oxygen source may include a cylinder of compressed oxygen. In other embodiments, the oxygen source may be the earth's atmosphere. In various such other embodiments, the oxygen source may include a concentrator to increase the level of oxygen in the oxygen flow supplied to the ozone generator.

The ozone generator 140 may be configured to convert the oxygen flow into ozone flow by any appropriate technology as previously described. Once the level of ozone in the oxygen flow reaches a level appropriate for use in a sterilization process it may be exhausted from the ozone generator 140, as an ozone flow into the treatment chamber 102 at the first end 124 thereof, and may be removed from the treatment chamber 102 at second end 126 thereof.

In some embodiments, the ozone flow may be removed from the treatment chamber 102 using a fan 150. In one embodiment, the fan 150 is located in close proximity to the output opening 126 to provide a negative pressure inside of the treatment chamber 102. In this manner, the fan 150 may create a negative pressure within the treatment chamber 102 sufficient to cause the ozone introduced at the first end 124 of the treatment chamber 102 to be drawn through the treatment chamber and to exit in a safe and efficient manner from the second end 126 of the chamber. In some embodiments, the fan 150 may also include a filter or ozone destructor 160. The filter or ozone destructor 160 may be configured to convert ozone into oxygen in a known manner. The filter or ozone destructor 160 may be configured to remove toxicity from the exhaust flow before it is emitted into the atmosphere A. In various embodiments, the filter or ozone destructor 160 may receive an exhaust flow containing high levels of ozone from the treatment chamber 102 via output port 112. The filter or ozone destructor 160 may be configured to convert ozone in the exhaust flow back into oxygen. The oxygen may then be released back into the atmosphere A. By converting ozone back into oxygen before releasing it into the atmosphere A, pollution generated by the continuous flow sterilization system 100 can be reduced or eliminated. In some embodiments, the filter or ozone destructor 160 may expose ozone to a catalyst, causing the ozone ($O_3$) to lose an atomic oxygen (O) and to revert back to oxygen ($O_2$) for release into the atmosphere A. The atmosphere A may refer to the earth's atmosphere, the atmosphere within an enclosed space such a building, or the like. In some embodiments, the filter or ozone destructor 160 may include a carbon filter.

As previously mentioned, the treatment chamber 102 may include first and second ends 124, 126. An input port 108 and input opening 110 may be located proximate the first end 124 of the treatment chamber 102. An output port 112 and output opening 114 may be located proximate the second end 126 of the treatment chamber 102. The embodiments are not limited in this context. Thus, it will be appreciated that although the description will proceed in the context of a treatment chamber 102 comprising an elongated cylinder, that the treatment chamber can assume any shape, size or configuration to provide desired sterilization of bulk material moved therethrough.

The treatment chamber 102 may enclose a volume of space within which contents of the enclosed volume may be safely and efficiently sterilized via the introduction of ozone (O3) via the ozone generator 140. A portion of the enclosed volume may contain the gaseous form of ozone (e.g., ozone flow) introduced via the ozone generator 140. Bulk material may be received within the treatment chamber 102 via the input opening 110. In some embodiments, the input opening 110 includes a funnel 111 to guide contents into the treatment chamber 102.

The contents of the treatment chamber 102, such as a bulk material may be exposed to predetermined concentrations of ozone in its gaseous form. In various embodiments the level of ozone within the treatment chamber 102 may be monitored and controlled during the sterilization process.

The level of ozone in the treatment chamber 102 may be controlled via the rate of introduction of the ozone flow and/or the rate of ozone removal via the output port 112.

In some embodiments, the contents of the treatment chamber 102 (e.g., treated bulk material) may exit the treatment chamber 102 via output opening 114. In some embodiments, a receiving tray (not shown) may be located below the output opening 114 to catch or otherwise direct bulk material exiting the treatment chamber 102.

As previously mentioned, the treatment chamber 102 may enclose at least a portion of an auger 116. In some embodiments, the auger 116 may generally extend from the input opening 110 to the output opening 114. The auger 116 may be configured to move bulk material introduced into the chamber 102 via the input opening 110 towards the output opening 114. In some embodiments, the auger 116 may be a helical screw rotatably disposed within the treatment chamber 102, and mounted on a rotatable shaft 110. In various embodiments, the auger 116 may be formed from a polymer such as a plastic, which can resist oxidizing effects of ozone. As previously mentioned, in one embodiment, the outer diameter of the auger 116 (e.g., the outer diameter of the helical screw) is substantially similar to the inner diameter of the treatment chamber 102 in which the auger 116 resides. That is, preferably, the outer edge of the auger 116 is in very close proximity to the inner surface of the treatment chamber 102. In this manner, the ozone flow traveling from the input port 108 to the output port 112 is prevented from passing between the outer edge of the augur 116 and the inner diameter of the treatment chamber 102, thus forcing the ozone to mix with the bulk material. That is, the amount of ozone flow that can travel from the input port 108 to the output port 112, above the bulk material, without mixing with the bulk material is substantially minimized or eliminated.

The shaft 170 may include first and second ends 172, 174. A drive motor 176 may be coupled to the shaft 170 proximate the second end 174. In various embodiments, the drive motor 176 may rotate the auger 116 within the treatment chamber 102 in a first or second rotational direction in order to move bulk material within the treatment chamber 102 in a desired direction. In addition, one exemplary non-liming embodiment, bulk material within the treatment chamber 102 may be moved from the input opening 110 to the output opening 114 with an auger 116 connected to a variable speed drive motor 176 to enable variations in rotational speed and thus variations in the speed with which the bulk material is moved through the treatment chamber. In some embodiments, the drive motor 176 may change its direction of motion, thereby reversing movement of bulk material within the chamber 102. This can provide variability in dwell time and/or mixing of the feed in the chamber to test levels of ozone exposure. By incorporating a variable speed drive motor 176, bulk materials can move from the first end 124 of the treatment chamber 102 to the second end 126 of the treatment chamber 102 at a controlled rate.

As previously mentioned, the continuous flow sterilization system 100 may include a support structure 200 for supporting the continuous flow sterilization system 100. The support assembly 200 can be any support assembly now known or hereafter developed for securing the continuous flow sterilization system 100. For example, referring to FIGS. 2A-3, the support structure 200 may include a floor assembly 210, a chamber holding assembly 220, and a connection assembly 240 located therebetween. In use, the chamber holding assembly 220 is arranged and configured to hold and support the treatment chamber 102 thereon. For example, as shown, the chamber holding assembly 220 may include first and second longitudinal members 222, 224 for coupling to, either directly or indirectly, to the treatment chamber 102. For example, as shown, the first and second longitudinal members 222, 224 may be fastened to the drive motor 176. The floor assembly 210 may, for example, include interconnecting support member such as, first, second, and third members 214a, 214b, 214c, respectively, for receiving first, second, third and fourth feet 212a-d. Meanwhile the connection assembly 240 may include, for example, interconnecting posts 242 for coupling the floor assembly 210 to the sterilization holding assembly 220.

In use, the support assembly 200 is arranged and configured to enable the angle of inclination of the treatment chamber 102 and the auger 116 located thereon, to be adjusted. That is, the treatment chamber 102 may include a longitudinal axis X-X. The relative position of the treatment chamber 102, and specifically, the longitudinal axis X-X, may be adjusted with respect to a horizontal plane (noted by line H-H). In one embodiment, the support assembly 200 may be adjustable to enable the angle of inclination "a" may be adjusted between about 0 degrees to about 90 degrees. In this manner, the continuous flow sterilization system 100 can ensure that any bulk material that is received within the treatment chamber 102 via the input opening 110 is collected and tightly packed at the first end 124 of the treatment chamber 102 where it is gathered and moved by the auger 116. The angle of inclination can be manually or automatically controlled by any mechanism now known or hereafter developed. For example, as shown, a plurality of openings 225 may be formed in the first and second longitudinal members 222, 224 for receiving a fastener 226 extending thru the connection assembly 240. However, other mechanisms are envisioned including, for example, a motorized adjustment mechanism.

Although not shown, it will be appreciated that temperature sensors, humidity sensors, ozone concentration sensors can be implemented in the disclosed system in order to allow a user to monitor and control a sterilization operation using the disclosed system. In addition, one or more of these sensors may be coupled to or may otherwise communicate with control logic, such as a processor, to enable automated monitoring and control of the disclosed system.

Some embodiments of the disclosed device may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable line-level, low-level, object-oriented, visual, compiled and/or interpreted programming language.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision additional modifications, features, and advantages within the scope and spirit of the claims appended hereto.

What is claimed is:

1. A method for continuous sterilization of a bulk material, comprising:
   generating a flow of ozone from an oxygen source;
   introducing the flow of ozone into a treatment chamber, wherein the treatment chamber has first and second ends, the flow of ozone introduced proximate the first end, the second end positioned above the first end so that the treatment chamber is inclined;
   contacting the flow of ozone with the bulk material as the bulk material is being moved through the treatment chamber;
   measuring an ozone level or a temperature within the treatment chamber;
   creating a negative pressure within the treatment chamber to exhaust the flow of ozone out of the treatment chamber proximate the second end; and
   adjusting a speed that the bulk material moves through the treatment chamber, at least in part, on the measured ozone level or temperature within the treatment chamber.

2. The method of claim 1, comprising sterilizing the bulk material as the bulk material is moved through treatment chamber with the flow of ozone, the sterilizing occurring through the contacting of the flow of ozone with the bulk material.

3. The method of claim 1, further comprising filtering the flow of ozone before the flow of ozone is released into the atmosphere.

4. The method of claim 1, further comprising determining an effectiveness of the treatment process using at least one of said measured ozone level and said measured temperature.

5. The method of claim 1, further comprising adjusting the flow of ozone into the treatment chamber to reach a saturation limit characteristic for the bulk material.

6. The method of claim 1, further comprising comparing an ozone concentration at an output of the treatment chamber with an ozone concentration at an input of the treatment chamber.

7. The method of claim 6, further comprising determining a sterilization of the bulk material is complete when the ozone concentration at the output of the treatment chamber is comparable with the ozone concentration at the input of the treatment chamber.

8. A method for continuous sterilization of a bulk material, comprising:
   generating a flow of ozone from an oxygen source;
   introducing the flow of ozone into a treatment chamber, wherein the treatment chamber has first and second ends, the flow of ozone introduced proximate the first end;
   contacting the flow of ozone with the bulk material as the bulk material is being moved through the treatment chamber;
   measuring at least one of an ozone level and a temperature within the treatment chamber; and
   creating a negative pressure within the treatment chamber to exhaust the flow of ozone out of the treatment chamber proximate the second end to thereby adjust an ozone concentration within the treatment chamber.

9. The method of claim 8, further comprising determining an effectiveness of the treatment process using at least one of said measured ozone level and said measured temperature.

10. The method of claim 8, further comprising adjusting the flow of ozone into the treatment chamber to reach a saturation limit characteristic for the bulk material.

11. The method of claim 8, further comprising comparing an ozone concentration at an output of the treatment chamber with an ozone concentration at an input of the treatment chamber.

12. The method of claim 11, further comprising determining a sterilization of the bulk material is complete when the ozone concentration at the output of the treatment chamber is comparable with the ozone concentration at the input of the treatment chamber.

* * * * *